(12) United States Patent
Watanabe

(10) Patent No.: US 11,051,737 B2
(45) Date of Patent: Jul. 6, 2021

(54) BIOMAGNETIC MEASUREMENT METHOD, BIOMAGNETIC MEASURING DEVICE, AND BIOMAGNETIC MEASURING SYSTEM

(71) Applicant: Taishi Watanabe, Tokyo (JP)

(72) Inventor: Taishi Watanabe, Tokyo (JP)

(73) Assignee: Ricoh Company, Ltd., Tokyo (JP)

(*) Notice: Subject to any disclaimer, the term of this patent is extended or adjusted under 35 U.S.C. 154(b) by 405 days.

(21) Appl. No.: 15/976,073

(22) Filed: May 10, 2018

(65) Prior Publication Data
US 2018/0333062 A1 Nov. 22, 2018

(30) Foreign Application Priority Data

May 19, 2017 (JP) .............................. JP2017-100001
Mar. 28, 2018 (JP) .............................. JP2018-062936

(51) Int. Cl.
*A61B 5/242* (2021.01)
*A61B 5/11* (2006.01)
(Continued)

(52) U.S. Cl.
CPC ............ *A61B 5/242* (2021.01); *A61B 5/1104* (2013.01); *A61B 5/24* (2021.01); *A61B 5/4884* (2013.01);
(Continued)

(58) Field of Classification Search
CPC ....... A61B 5/6824; A61B 5/70; A61B 5/1104; A61B 5/7214; A61B 5/04005; A61B 5/4884; A61B 5/04001
See application file for complete search history.

(56) References Cited

U.S. PATENT DOCUMENTS 3,715,654 A * 2/1973 Scarzello ............. G01R 33/022
324/301
4,595,018 A * 6/1986 Rantala ................ A61B 5/7217
600/546
(Continued)

FOREIGN PATENT DOCUMENTS

JP 2008-538956 11/2008
JP 2018-057843 4/2018
(Continued)

OTHER PUBLICATIONS

Nakayama ["Real-time Measurement of Biomagnetic Vector Fields in Functional Syncytium Using Amorphous Metal" Scientific Reports, Sensors and Probes, Biomedical Engineering, 2015] (Year: 2015).*
(Continued)

*Primary Examiner* — Oommen Jacob
(74) *Attorney, Agent, or Firm* — Oblon, McClelland, Maier & Neustadt, L.L.P.

(57) ABSTRACT

A biomagnetic measurement method, a biomagnetic measuring device, and a biomagnetic measuring system. The method and the biomagnetic measuring device includes obtaining first measurement data output from a magnetic field detector upon giving a stimulus to a subject in a first state where a site of interest of the subject is made close to the magnetic field detector, and obtaining second measurement data output from the magnetic field detector upon giving a stimulus to the subject in a second state where a site to which the stimulus is given and a position of the site to which the stimulus is given are equivalent to a site to which the stimulus is given and a position of the site to which the stimulus is given in the first state, respectively, and the site of interest of the subject is separated from the magnetic field detector with reference to the first state.

10 Claims, 14 Drawing Sheets

(51) Int. Cl.
*A61B 5/00* (2006.01)
*A61B 5/24* (2021.01)

(52) U.S. Cl.
CPC .............. *A61B 5/6824* (2013.01); *A61B 5/70* (2013.01); *A61B 5/7214* (2013.01)

(56) References Cited

U.S. PATENT DOCUMENTS

| | | | | |
|---|---|---|---|---|
| 4,690,149 A * | 9/1987 | Ko | ........................ | A61B 5/0507 600/409 |
| 4,793,355 A * | 12/1988 | Crum | ................. | A61B 5/04008 324/201 |
| 4,827,217 A * | 5/1989 | Paulson | .............. | A61B 5/04005 324/201 |
| 4,913,152 A * | 4/1990 | Ko | ..................... | A61B 5/04005 324/248 |
| 4,945,305 A * | 7/1990 | Blood | ....................... | G01B 7/14 324/207.17 |
| 4,971,060 A * | 11/1990 | Schneider | .......... | A61B 5/04005 378/162 |
| 4,977,896 A * | 12/1990 | Robinson | ........... | A61B 5/04005 324/245 |
| 5,020,538 A * | 6/1991 | Morgan | .............. | A61B 5/04008 128/901 |
| 5,131,401 A * | 7/1992 | Westenskow | ........ | A61B 5/1106 600/554 |
| 5,220,921 A * | 6/1993 | Ferris | ................. | A61B 5/04009 324/248 |
| 5,351,687 A * | 10/1994 | Kroll | .................. | A61B 5/04007 600/409 |
| 5,425,382 A * | 6/1995 | Golden | .................... | A61B 5/06 128/899 |
| 5,444,372 A * | 8/1995 | Wikswo, Jr. | ........ | G01R 33/0358 324/248 |
| 5,458,142 A * | 10/1995 | Farmer | .................... | A61N 2/02 600/409 |
| 5,644,229 A * | 7/1997 | Dossel | ............... | G01R 33/0206 324/244 |
| 5,730,131 A * | 3/1998 | Ohyu | ................. | A61B 5/04005 600/407 |
| 5,752,512 A * | 5/1998 | Gozani | .................... | A61B 5/05 600/347 |
| 5,752,514 A * | 5/1998 | Okamura | ........... | A61B 5/04005 324/244 |
| 5,792,212 A * | 8/1998 | Weijand | ................... | A61B 5/04 600/554 |
| 5,851,191 A * | 12/1998 | Gozani | ................ | A61B 5/0488 600/554 |
| 5,895,871 A * | 4/1999 | Patton | ................ | A61B 5/04005 73/866.5 |
| 6,032,072 A * | 2/2000 | Greenwald | .......... | A61B 5/0478 600/383 |
| 6,129,678 A * | 10/2000 | Ryan | ...................... | A61B 5/044 600/515 |
| 6,263,230 B1 * | 7/2001 | Haynor | .................. | A61B 5/062 128/899 |
| 6,356,781 B1 * | 3/2002 | Lee | ........................ | A61B 5/162 324/309 |
| 6,370,416 B1 * | 4/2002 | Rosenfeld | ............ | G01R 33/56 128/922 |
| 6,428,484 B1 * | 8/2002 | Battmer | ............... | A61B 5/6817 600/554 |
| 6,538,436 B1 * | 3/2003 | Simola | .................. | G01D 3/032 324/225 |
| 6,894,492 B1 * | 5/2005 | Dziech | ................. | G01B 7/003 324/238 |
| 7,340,125 B1 * | 3/2008 | Doty | ................... | G02B 6/3574 385/140 |
| 7,738,944 B2 * | 6/2010 | Ho | ................... | G01R 33/56375 600/415 |
| 2001/0029329 A1 * | 10/2001 | Avrin | ..................... | G01R 33/16 600/407 |
| 2002/0183647 A1 * | 12/2002 | Gozani | ................ | A61B 5/0492 600/554 |
| 2003/0032889 A1 * | 2/2003 | Wells | ................... | A61B 5/4041 600/546 |
| 2003/0153824 A1 * | 8/2003 | Tsubata | ................ | A61B 8/4227 600/407 |
| 2005/0033154 A1 * | 2/2005 | deCharms | .......... | G01R 33/4806 600/410 |
| 2005/0057246 A1 * | 3/2005 | Orozco | ................ | G01R 31/311 324/228 |
| 2005/0065422 A1 * | 3/2005 | Kandori | ............... | A61B 5/4082 600/407 |
| 2005/0073322 A1 * | 4/2005 | Hibbs | .................... | G01R 33/02 324/658 |
| 2005/0092483 A1 * | 5/2005 | Vinegar | ................. | E21B 43/305 166/60 |
| 2005/0212515 A1 * | 9/2005 | Watanabe | .......... | A61B 5/04007 324/248 |
| 2006/0276702 A1 * | 12/2006 | McGinnis | ............ | A61B 5/6848 600/372 |
| 2007/0038067 A1 * | 2/2007 | Kandori | ............... | A61B 5/1124 600/409 |
| 2008/0070267 A1 * | 3/2008 | Spitzer | ..................... | A61P 25/16 435/29 |
| 2008/0161190 A1 * | 7/2008 | Kim | ................... | G01R 33/0354 505/162 |
| 2008/0262372 A1 * | 10/2008 | Manto | ................. | A61B 5/1121 600/546 |
| 2009/0012384 A1 * | 1/2009 | Adachi | ................ | A61B 5/6822 600/409 |
| 2009/0062676 A1 * | 3/2009 | Kruglikov | ............ | A61B 5/0484 600/544 |
| 2009/0062685 A1 * | 3/2009 | Bergethon | ........... | A61B 5/4041 600/554 |
| 2009/0177247 A1 * | 7/2009 | Neal | ..................... | A61N 1/36038 607/57 |
| 2010/0219819 A1 * | 9/2010 | Kimura | ................... | G01Q 60/50 324/244 |
| 2010/0292606 A1 * | 11/2010 | Prakash | ............. | A61B 5/04012 600/554 |
| 2012/0053483 A1 * | 3/2012 | Doidge | ................ | A61B 5/4827 600/544 |
| 2014/0135602 A1 * | 5/2014 | Lemke | ................. | A61B 5/0205 600/324 |
| 2015/0321000 A1 * | 11/2015 | Rosenbluth | ............ | A61N 1/025 607/48 |
| 2018/0092561 A1 | 4/2018 | Kawabata et al. | | |
| 2018/0333062 A1 * | 11/2018 | Watanabe | ........... | A61B 5/6824 |
| 2018/0369568 A1 * | 12/2018 | Ishibe | ................. | A61N 1/0456 |
| 2019/0125269 A1 * | 5/2019 | Markovic | ................ | A61N 1/18 |

FOREIGN PATENT DOCUMENTS

WO WO2006/114473 A1 11/2006
WO WO2010/103866 A1 9/2010

OTHER PUBLICATIONS

McGill ["On the Nature and Elimination of Stimulus Artifact in Nerve Signals Evoked and Recorded Using Surface Electrodes" IEEE Transactions on Biomedical Engineering, 1982], (Year: 1982).*

Taishi Watanabe, et al., "Removal of Stimulus-Induced Artifacts in Functional Spinal Cord Imaging" 35th Annual International Conference of the IEEE EMBS Osaka, Japan, Jul. 3-7, 2013, pp. 3391-3394.

* cited by examiner

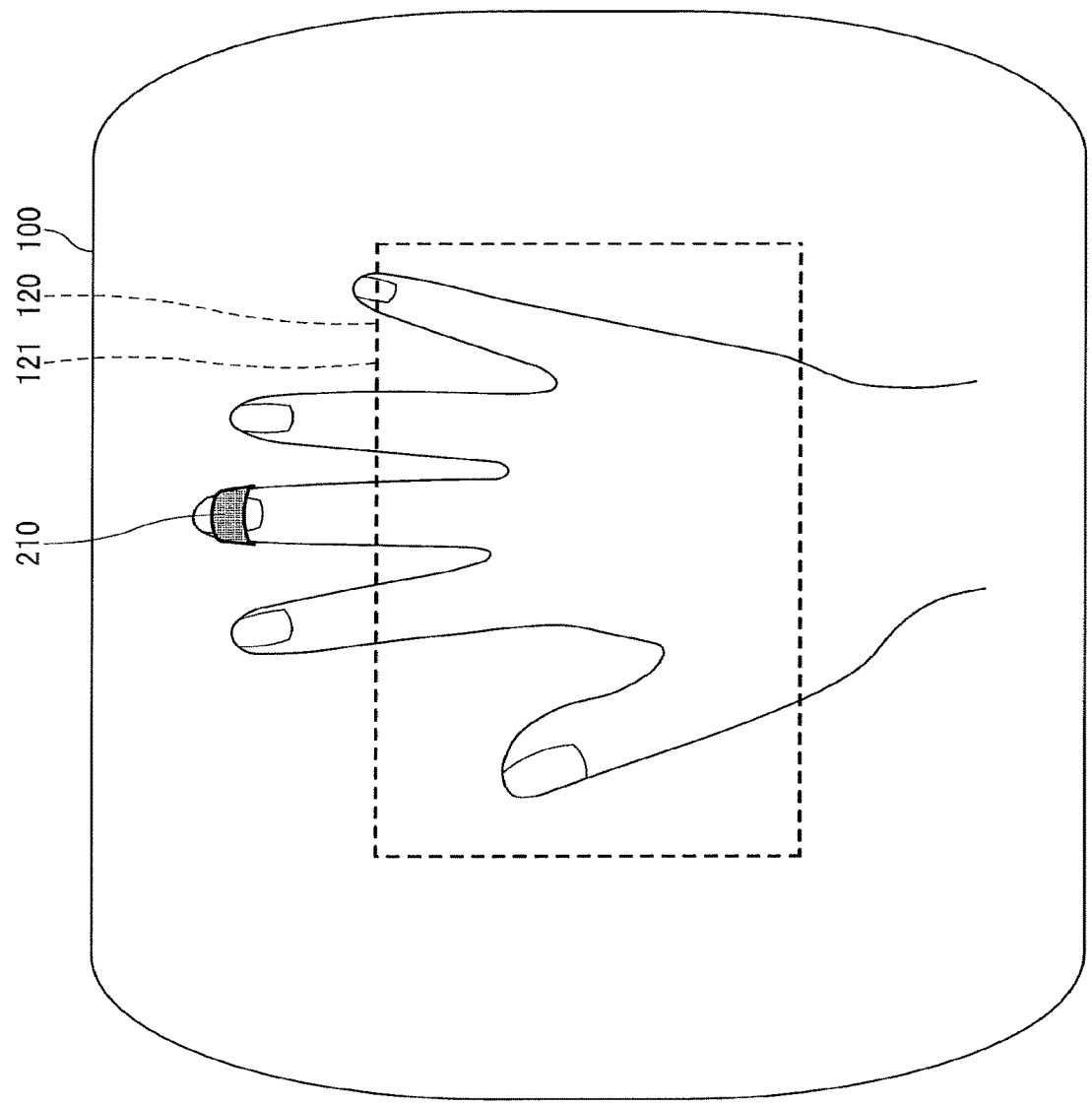

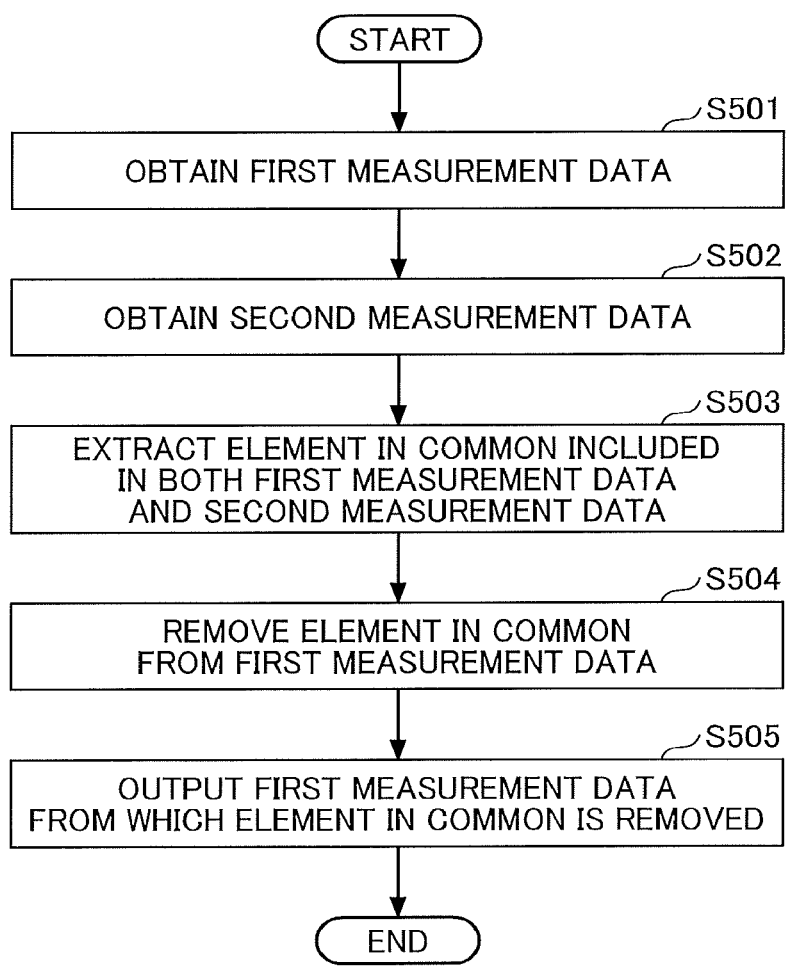

# BIOMAGNETIC MEASUREMENT METHOD, BIOMAGNETIC MEASURING DEVICE, AND BIOMAGNETIC MEASURING SYSTEM

CROSS-REFERENCE TO RELATED APPLICATIONS

This patent application is based on and claims priority pursuant to 35 U.S.C. § 119(a) to Japanese Patent Application Nos. 2017-100001 and 2018-062936, filed on May 19, 2017, and Mar. 28, 2018, respectively, in the Japan Patent Office, the entire disclosures of which are hereby incorporated by reference herein.

BACKGROUND

Technical Field

Embodiments of the present disclosure relate to a biomagnetic measurement method, a biomagnetic measuring device, and a biomagnetic measuring system.

Background Art

Conventionally, biomagnetic measurement is known in the art in which stimuli are given to a part of a test object to induce the nerve activity at a to-be-measured site and the magnetic field that is emitted from this nerve activity is measured using a sensor. In such biomagnetic measurement, interference magnetic-field signals are induced by, for example, stimuli or the movement of muscles caused by the stimuli, and such interference magnetic-field signals become noise.

In view of the above circumstances, currently, technologies to remove an interference magnetic-field signal are under development. As such technologies, for example, the dual signal subspace projection (DSSP) is known in the art.

SUMMARY

Embodiments of the present disclosure described herein provide a biomagnetic measurement method, a biomagnetic measuring device, and a biomagnetic measuring system. The biomagnetic measurement method includes obtaining first measurement data output from a magnetic field detector upon giving a stimulus to a subject in a first state where a site of interest of the subject is made close to the magnetic field detector, obtaining second measurement data output from the magnetic field detector upon giving a stimulus to the subject in a second state where a site to which the stimulus is given and a position of the site to which the stimulus is given are equivalent to a site to which the stimulus is given and a position of the site to which the stimulus is given in the first state, respectively, and the site of interest of the subject is separated from the magnetic field detector with reference to the first state, and outputting a signal of interest from which an interference magnetic-field signal component in the first measurement data induced by the stimulus has been removed using second measurement data. The biomagnetic measuring device and the biomagnetic measuring system include a magnetic field detector to measure a magnetic field, an acquisition unit to obtain first measurement data output from the magnetic field detector upon giving a stimulus to a subject in a first state where a site of interest of the subject is made close to the magnetic field detector and second measurement data output from the magnetic field detector upon giving a stimulus to the subject in a second state where a site to which the stimulus is given and a position of the site to which the stimulus is given are equivalent to a site to which the stimulus is given and a position of the site to which the stimulus is given in the first state, respectively, and the site of interest of the subject is separated from the magnetic field detector with reference to the first state, and an analyzer to output a signal of interest from which an interference magnetic-field signal component in the first measurement data induced by the stimulus has been removed using the second measurement data.

BRIEF DESCRIPTION OF THE DRAWINGS

A more complete appreciation of exemplary embodiments and the many attendant advantages thereof will be readily obtained as the same becomes better understood by reference to the following detailed description when considered in connection with the accompanying drawings.

FIG. 2 is a diagram illustrating the relative positions of a measurable area and the source of an interference magnetic-field signal, according to the first embodiment of the present disclosure.

FIG. 5 is a flowchart of the processes that are performed by an analyzer of a biomagnetic field measuring device, according to the first embodiment of the present disclosure.

Figure 1A:
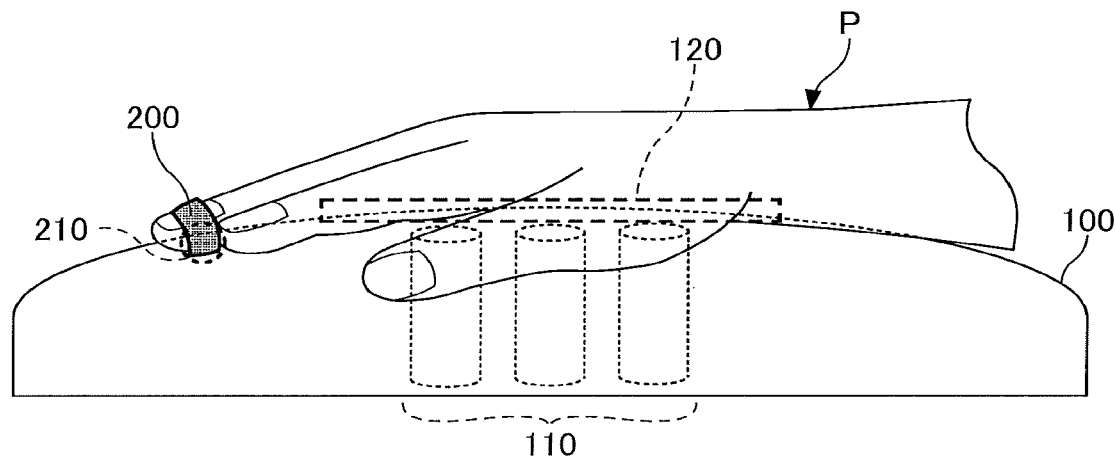
FIG. 1A and FIG. 1B are diagrams each illustrating biomagnetic measurement using a biomagnetic field measuring device, according to a first embodiment of the present disclosure.

The accompanying drawings are intended to depict exemplary embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments shown in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

First Embodiment

A first embodiment of the present disclosure is described below with reference to the accompanying drawings.

Figure 1B:
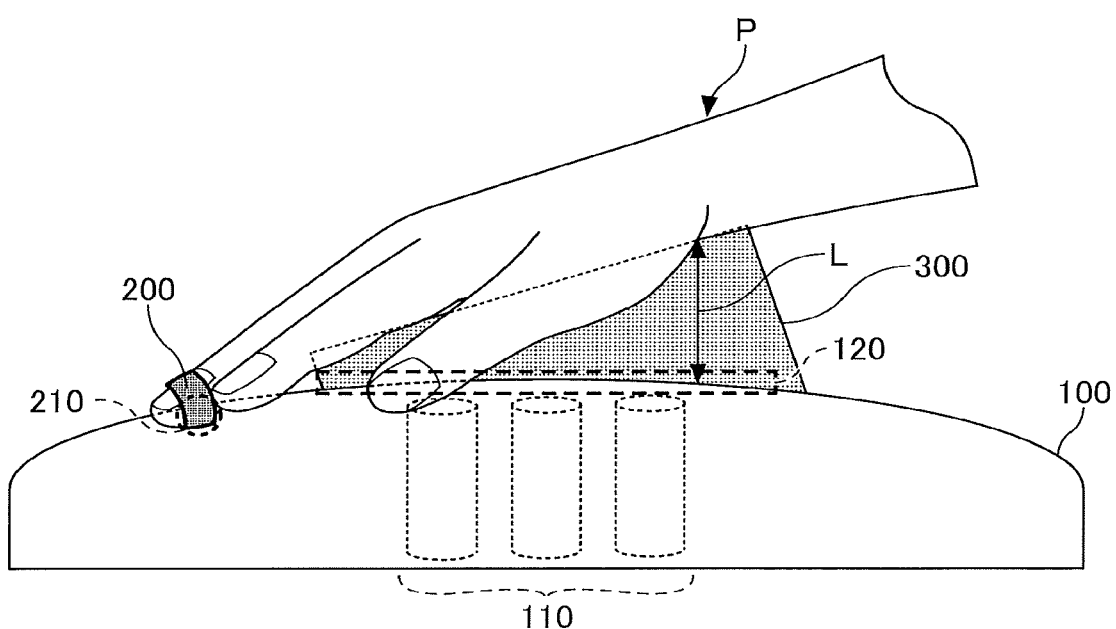

FIG. 1A and FIG. 1B are diagrams each illustrating biomagnetic measurement using a biomagnetic field measuring device 100 according to the first embodiment.

FIG. 1A is a diagram illustrating the first measurement to obtain the first measurement data, according to the present embodiment.

FIG. 1B is a diagram illustrating the second measurement to obtain the second measurement data, according to the present embodiment.

The biomagnetic field measuring device 100 according to the present embodiment is provided with a magnetic field detector 110, and measures the magnetic field caused by the electrical signals indicating the activities of the nerves at a to-be-measured site of a test object P, which are caused by a stimulus impressed by the nerve stimulator 200.

The nerve stimulator 200 according to the present embodiment may be, for example, a belt onto which an electrode is fixed. In such a configuration, the test object P is wrapped with a belt, and the nerve stimulator 200 is mounted such that the electrode touches the test object P. Accordingly, the position of the electrode is fixed. The nerve stimulator 200 generates a stimulus under predetermined stimulus conditions. The stimulus conditions will be described later in detail.

As illustrated in FIG. 1A, in the biomagnetic field measuring device 100 according to the present embodiment, the test object P touches an area 120 where the magnetic field is measurable by the magnetic field detector 110, and the magnetic field is measured at the to-be-measured site of the test object P upon giving stimuli to the test object P by the nerve stimulator 200.

In the following description of the present embodiment, the area 120 on the housing of the biomagnetic field measuring device 100 where the magnetic field is measurable by the magnetic field detector 110 is referred to as a measurable area 120.

In the following description of the present embodiment, the procedure of giving a stimulus to the test object P by the nerve stimulator 200 in a state (first state) in which the test object P is made closest to the measurable area 120 (or the magnetic field detector 110) as illustrated in FIG. 1A and measuring the magnetic field is referred to as the first measurement procedure. Further, in the following description of the present embodiment, the data that is measured under the first measurement procedure is referred to as the first measurement data, and the to-be-measured site of the test object P is referred to as a site of interest.

The first measurement data according to the present embodiment indicates the magnetic-field (magnetic flux density), caused as the magnetic field signal that originates from the nerve activity at the site of interest of the test object P and an interference magnetic-field signal caused by stimuli or the like given by the nerve stimulator 200 are superposed on each other. In this configuration, the source of an interference magnetic-field signal is a contact surface (source) 210 where the electrode of the nerve stimulator 200 contacts the test object P.

Next, in the present embodiment, as illustrated in FIG. 1B, a stimulus same as that of the first measurement procedure is given in a state where the measurable area 120 is separated from the site of interest (second state) without changing the position of the source 210 of an interference magnetic-field signal from that of the first measurement procedure, and the magnetic field is measured at the site of interest of the test object P.

In the following description of the present embodiment, this measurement procedure is referred to as the second measurement procedure, and the data that is measured under the second measurement procedure is referred to as the second measurement data.

In other words, in the second measurement procedure according to the present embodiment, the magnetic field is measured at the site of interest in the second state where the site of interest is separated from the measurable area 120, where the site to which a stimulus is given is same as that of the first state and the position of the site to which the stimulus is given is also the same as that of the first state.

In the second measurement procedure according to the present embodiment, the site of interest is separated from the measurable area 120. Accordingly, the distribution of the magnetic field signal that originates from the nerve activity at the site of interest varies from the first measurement data. By contrast, the source 210 of an interference magnetic-field signal is the contact surface same as that of the first measurement procedure. Due to this configuration, the distribution of the interference magnetic-field signals remains unchanged. In other words, in the first measurement procedure and the second measurement procedure, the relative positions of the contact surface that serves as the source 210 of an interference magnetic-field signal and the magnetic field detector 110 remain unchanged. Due to this configuration, the distribution of the interference magnetic-field signals remain unchanged.

Due to this configuration, the second measurement data indicates the magnetic-field (magnetic flux density) where a magnetic-field signal whose distribution is different from that of the magnetic field signal in the first measurement procedure that originates from the nerve activity and an interference magnetic-field signal having the distribution same as that of an interference magnetic-field signal in the first measurement procedure are superimposed on top of one another.

The intensity of an electrical signal in the second measurement procedure may be significantly small and even ignorable, compared with the intensity of an interference magnetic-field signal. In such cases, it may be considered that the second measurement data mainly accounts for the interference magnetic-field signal.

In the present embodiment, the signal component of an interference magnetic-field signal is removed from the first measurement data using the first measurement data and the second measurement data. By so doing, the magnetic-field signal component that originates from the nerve activity at the site of interest is extracted.

In the following description of the present embodiment, the magnetic field signal that originates from the nerve activity at the site of interest is referred to as a signal of interest. In other words, the biomagnetic field measuring device 100 according to the present embodiment obtains a signal of interest by removing the signal component of an interference magnetic-field signal from the first measurement data.

As described above, in the biomagnetic field measuring device 100 according to the present embodiment, the signals of interest from which the interference due to the interference magnetic-field signals have been removed are obtained, using the first measurement data and the second measurement data where the distribution of magnetic field is different from each other with reference to the test object P.

Due to this configuration according to the present embodiment, it is satisfactory as long as the first measurement procedure and the second measurement procedure can be performed without changing the relative positions of the source 210 of an interference magnetic-field signal and the magnetic field detector 110, and it is not necessary to limit the relative positions of the site of interest and the source 210 of an interference magnetic-field signal.

Accordingly, with the present embodiment, the interference from an interference magnetic-field signal can be canceled even when the source 210 of an interference magnetic-field signal is disposed near the site of interest. Moreover, in the present embodiment, even when the source 210 of an interference magnetic-field signal is disposed within the measurable area 120 of the magnetic field detector 110, the interference from an interference magnetic-field signal can be canceled. Accordingly, with the present embodiment, the accuracy of the measurement in a biomagnetic field improves.

On the biomagnetic field measuring device 100 according to the present embodiment, a supporting member 300 that supports the test object P, which is used in the second measurement procedure, may be provided in order to separate the test object P and the measurable area 120 from each other without displacing the source 210 of an interference magnetic-field signal.

For example, the supporting member 300 may removably be held on the housing of the biomagnetic field measuring device 100, and may be inserted between the measurable area 120 and the test object P when measurement is performed under the second measurement procedure.

In the present embodiment as illustrated in FIG. 1A and FIG. 1B, the test object P is a human hand, and the site of interest is a palm. Moreover, the site to which a stimulus is given by the nerve stimulator 200 is around the first knuckle joint of a middle finger.

As described above, the configuration according to the present embodiment may be applied to cases in which a site of interest and a site to which a stimulus is given are close to each other. In other words, according to the present embodiment, even when the source 210 of an interference magnetic-field signal is disposed near the measurable area 120 of the magnetic field detector 110, the interference in the biomagnetic field caused to the site of interest from an interference magnetic-field signal can be canceled.

In the present embodiment as illustrated in FIG. 1A and FIG. 1B, the site of interest is in full contact with the measurable area 120 in the first measurement procedure, and the site of interest is separated from the measurable area 120 in the second measurement procedure. However, no limitation is intended thereby.

In the present embodiment, it is configured such that the distance between the measurable area 120 and the position of the site of interest in the second measurement procedure is longer than the distance between the measurable area 120 and the position of the site of interest in the first measurement procedure.

In other words, in the present embodiment, it is satisfactory as long as the distance between the site of interest and the measurable area 120 under the second measurement procedure is longer than the distance between the site of interest and the measurable area 120 under the first measurement procedure. Accordingly, in the first measurement procedure, it is not necessary for the site of interest to touch the measurable area 120.

Next, the relative positions of the measurable area 120 and the source 210 of an interference magnetic-field signal is described with reference to FIG. 2.

FIG. 2 is a diagram illustrating the relative positions of the measurable area 120 and the source 210 of an interference magnetic-field signal, according to the first embodiment.

FIG. 2 is a top view of the illustration of FIG. 1A. In this configuration, an approximate distance between the palm of a hand of the test object P, which is the site of interest, and the first knuckle joint of a middle finger is about 5 centimeters (cm). Accordingly, the distance between the boundary of the measurable area 120 and the source 210 of an interference magnetic-field signal in the example as illustrated in FIG. 2 is also about 5 cm.

For example, in the present embodiment, the source 210 of an interference magnetic-field signal may be on a boundary 121 between the measurable area 120 and the outside of the measurable area 120, or may be disposed near the boundary 121. Alternatively, the source 210 of an interference magnetic-field signal may be disposed inside the measurable area 120.

Next, the biomagnetic field measuring device 100 according to the present embodiment is described with reference to FIG. 3.

Figure 3:
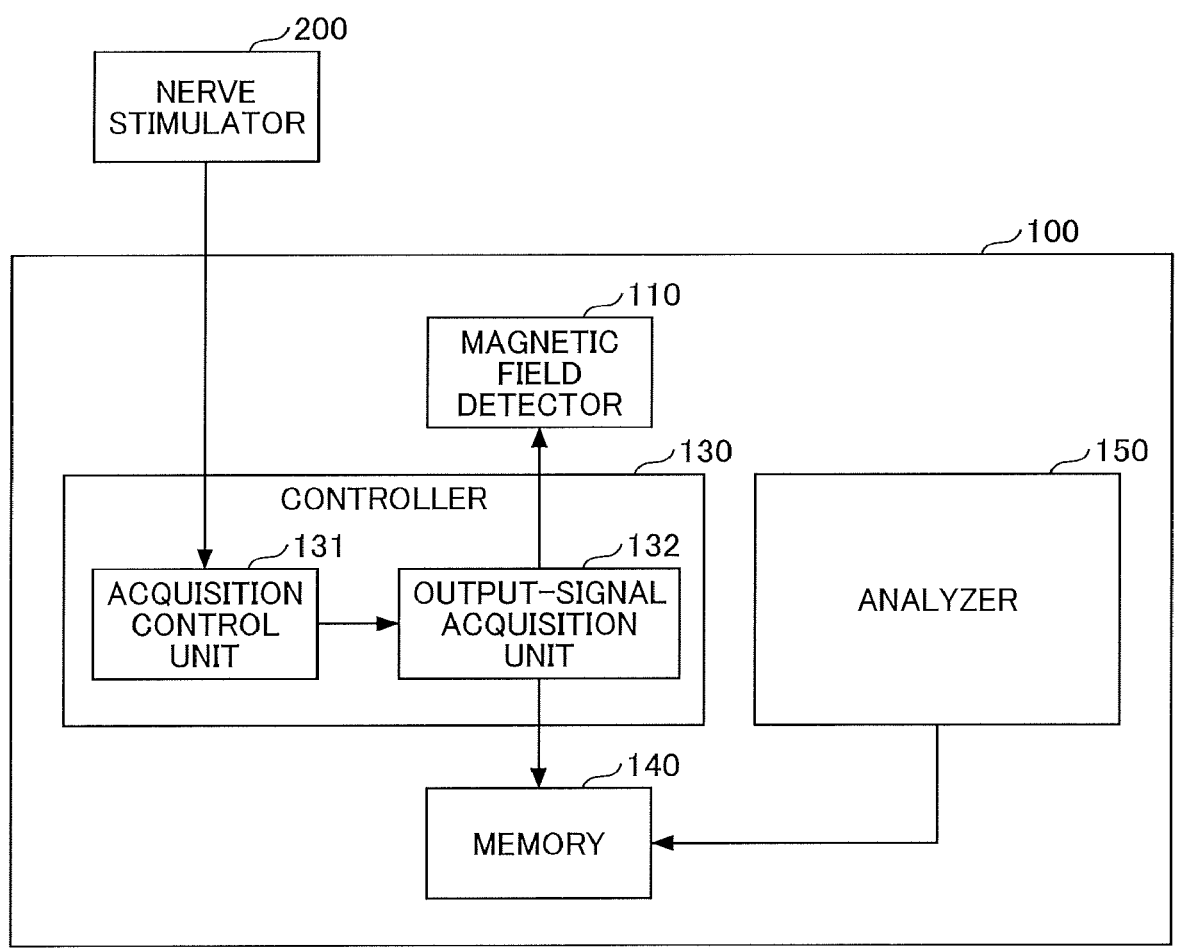
FIG. 3 is a diagram illustrating the functions of a biomagnetic field measuring device according to the first embodiment of the present disclosure.

FIG. 3 is a diagram illustrating the functions of the biomagnetic field measuring device 100 according to the first embodiment.

The biomagnetic field measuring device 100 according to the present embodiment includes a magnetic field detector 110, a controller 130, a memory 140, and an analyzer 150.

The magnetic field detector 110 according to the present embodiment includes, for example, a sensor array that detects the magnetic field and a driver device that drives the sensor array.

The controller 130 according to the present embodiment controls the measuring operation of the biomagnetic field measuring device 100. The controller 130 will be described later in detail. The memory 140 according to the present embodiment stores the measurement data obtained by the control performed by the controller 130. In particular, the memory 140 stores the first measurement data and the second measurement data.

The analyzer 150 according to the present embodiment obtains a signal of interest using the first measurement data and the second measurement data stored in the memory 140, and outputs the obtained signal of interest. The biomagnetic field measuring device 100 according to the present embodiment may be provided with a display, and the analyzer 150 may control the display to display the obtained signal of interest. The analyzer 150 according to the present embodiment may perform various kinds of analytical processing on the signal of interest, and may control the display to display the results of such analytical processing.

Next, the controller 130 according to the present embodiment is described. The controller 130 according to the present embodiment includes an acquisition control unit 131 and an output-signal acquisition unit 132.

Once a notification that application of stimuli to a site of interest has started is received from the nerve stimulator 200, the acquisition control unit 131 according to the present embodiment controls the output-signal acquisition unit 132 to obtain a signal output from the magnetic field detector 110.

Upon receiving an instruction to obtain a signal output from the acquisition control unit 131, the output-signal acquisition unit 132 starts obtaining the output signals output from the magnetic field detector 110, and stores the obtained output signals in the memory 140. In the present embodiment, the signals that are output from the magnetic field detector 110 are used as the first measurement data or the second measurement data.

In the biomagnetic field measuring device 100 according to the present embodiment, for example, the controller 130 may be implemented by a processor such as a central processing unit (CPU), and the memory 140 according to the present embodiment may be implemented by a storage device such as a memory. For example, the analyzer 150 according to the present embodiment may be implemented by an integrated circuit such as an application specific integrated circuit (ASIC).

Alternatively, the controller 130 and the analyzer 150 according to the present embodiment may be implemented by the same processor, such as by the single processor. The memory 140 according to the present embodiment may be, for example, a memory built into the processor that implements the controller 130.

Here, the stimulus conditions of the stimuli given to a site of interest by the nerve stimulator 200 according to the present embodiment are described.

For example, the stimuli according to the present embodiment may continuously be given to the site of interest for a predetermined length of time with a predetermined level of current. In such a configuration, the stimulus conditions include the frequency, the duration in time, and the values of the current. In particular, for example, the stimuli according to the present embodiment is a signal of 5 hertz (Hz) that continues for 0.3 millisecond (msec) with 4 milliampere (mA). The stimulus conditions according to the present embodiment may be edited as desired by a person who performs measurement using the biomagnetic field measuring device 100.

Note also that the stimuli according to the present embodiment may be other kinds of stimuli other than the electric current. For example, the stimuli according to the present embodiment may be given to the site of interest by magnetism.

Next, the operations of the biomagnetic field measuring device 100 according to the present embodiment are described with reference to FIG. 4.

Figure 4:
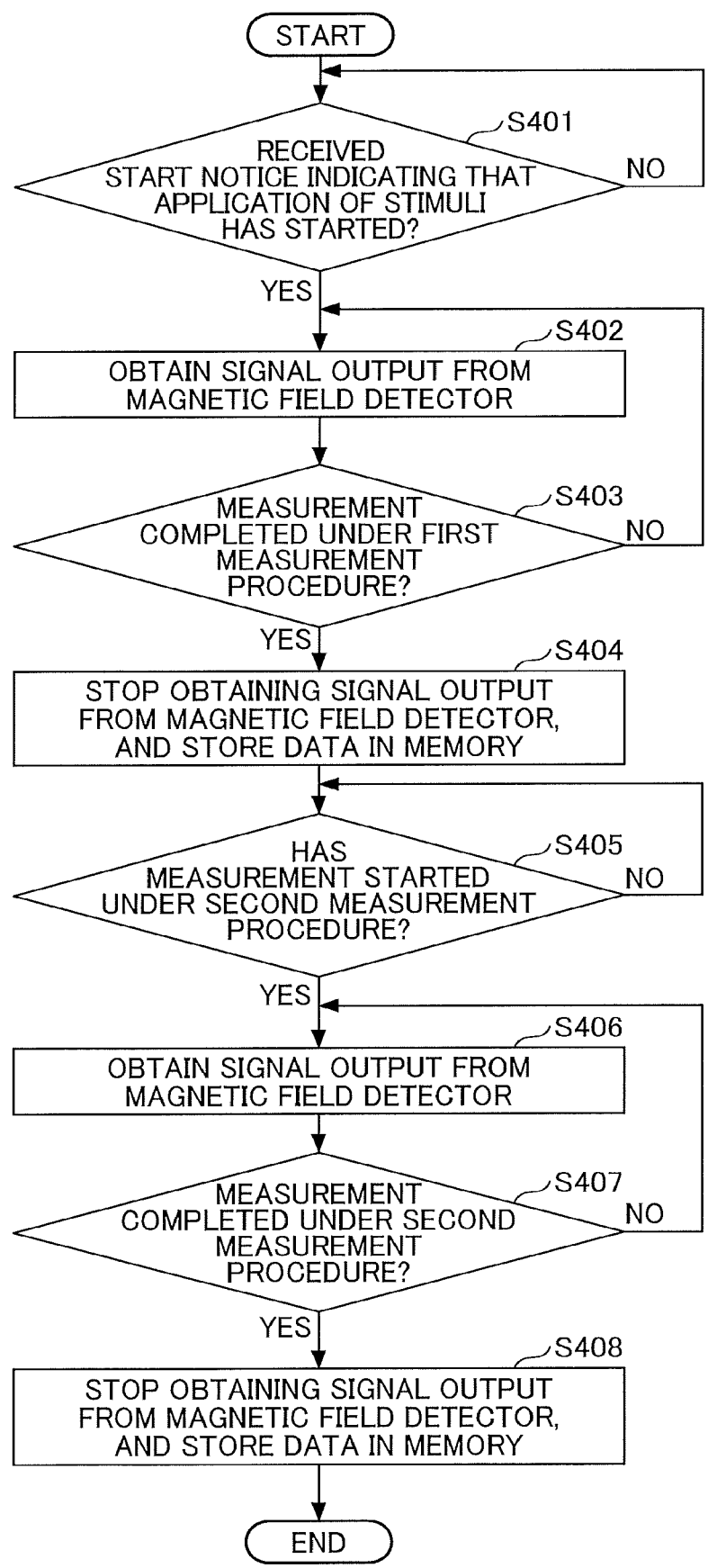
FIG. 4 is a flowchart of the operations of a biomagnetic field measuring device according to the first embodiment of the present disclosure.

FIG. 4 is a flowchart illustrating the operations of the biomagnetic field measuring device 100 according to the first embodiment.

In the present embodiment as illustrated in FIG. 4, the operations of the biomagnetic field measuring device 100 when measurement is firstly performed under the first measurement procedure and then measurement is performed under the second measurement procedure are described.

In the biomagnetic field measuring device 100 according to the present embodiment, the controller 130 determines whether or not the acquisition control unit 131 has received a start notice indicating that the application of stimuli has started (step S401). When it is determined that a start notice has not yet been received in the step S401 ("NO" in the step S401), the acquisition control unit 131 is on standby waiting until a start notice is received.

Once a start notice has been received in the step S401 ("YES" in the step S401), the controller 130 uses the acquisition control unit 131 to control the output-signal acquisition unit 132 to obtain an output signal, and the output-signal acquisition unit 132 obtains a signal output from the magnetic field detector 110 (step S402).

Subsequently, the controller 130 determines whether or not measurement has been completed under the first measurement procedure (step S403).

More specifically, the controller 130 according to the present embodiment may determine that the measurement under the first measurement procedure has been completed when the acquisition control unit 131 receives a notification that application of stimuli has ended from the nerve stimulator 200. Alternatively, in the present embodiment, it may be determined that the measurement under the first measurement procedure has been completed when stimuli are continuously given for a predetermined length of time. For example, such predetermined length of time in this configuration may be determined by the stimulus conditions.

When it is determined that measurement has not yet been completed under the first measurement procedure ("NO" in step S403), the controller 130 returns the process to the step S402.

When it is determined that measurement has been completed under the first measurement procedure ("YES" in step S403), the controller 130 uses the acquisition control unit 131 to control the output-signal acquisition unit 132 to stop obtaining an output signal, and the output-signal acquisition unit 132 stops obtaining an output signal. Then, the controller 130 stores the obtained output signal (i.e., the first measurement data) in the memory 140 (step S404).

Subsequently, the controller 130 determines whether or not measurement has started under the second measurement procedure (step S405). More specifically, when the acquisition control unit 131 has received a notification again that application of stimuli has started from the nerve stimulator 200, the controller 130 determines that measurement has started under the second measurement procedure.

When it is determined that measurement has not yet started under the second measurement procedure ("NO" in the step S405), the controller 130 is on standby waiting until a start notice is received.

When it is determined that measurement has started under the second measurement procedure ("YES" in the step S405), the controller 130 uses the acquisition control unit 131 to control the output-signal acquisition unit 132 to obtain an output signal, and the output-signal acquisition unit 132 obtains a signal output from the magnetic field detector 110 (step S406).

Subsequently, the controller 130 determines whether or not measurement has been completed under the second measurement procedure (step S407). The determination method in the step S407 is similar to that of the step S403 as described above.

When it is determined that measurement has not yet completed under the second measurement procedure ("NO" in step S407), the controller 130 returns the process to the step S406.

When it is determined that measurement has been completed under the second measurement procedure ("YES" in the step S407), the controller 130 uses the acquisition control unit 131 to control the output-signal acquisition unit 132 to stop obtaining an output signal, and the output-signal acquisition unit 132 stops obtaining an output signal. Then, the controller 130 stores the obtained output signal (i.e., the second measurement data) in the memory 140 (step S408), and terminates the processes.

In FIG. 4, after measurement is performed under the first measurement procedure, measurement is performed under the second measurement procedure. However, no limitation is intended thereby. In the biomagnetic field measuring device 100, measurement may be performed under the first measurement procedure after measurement is performed under the second measurement procedure.

Next, the processes that are performed by the analyzer 150 of the biomagnetic field measuring device 100 according to the present embodiment are described with reference to FIG. 5.

FIG. 5 is a flowchart of the processes that are performed by the analyzer 150 of the biomagnetic field measuring device 100, according to the first embodiment.

The analyzer 150 according to the present embodiment reduces the effect of an interference magnetic-field signal using the common-mode signal subspace projection (CSP) known in the art. In the CSP, the signal components that overlap with the measured values (noise) are removed using the data of noise.

In the present embodiment, the first measurement data corresponds to the measured values, and the second measurement data corresponds to the data that mainly accounts for the noise (components caused by an interference magnetic-field signal).

The analyzer 150 according to the present embodiment obtains from the memory 140 the first measurement data stored in the memory 140 (step S501), and then obtains the second measurement data (step S502).

In the processes depicted in FIG. 5, the first measurement data is firstly obtained and then the second measurement data is obtained. However, no limitation is intended thereby. The analyzer 150 may firstly obtain the second measurement data.

Subsequently, the analyzer 150 extracts an element in common included in both the first measurement data and the second measurement data (step S503).

Next, the analyzer 150 removes from the first measurement data the element in common extracted in the step S503 (step S504).

Next, the analyzer 150 outputs a signal obtained by removing the element in common from the first measurement data, as a signal of interest (step S505), and terminates the processes.

As described above, in the biomagnetic field measuring device 100 according to the present embodiment, in the second measurement procedure, the stimulus of the same stimulus conditions is given to the site same as the site to which a stimulus is given under the first measurement procedure. Accordingly, the second measurement data that mainly accounts for the interference magnetic-field signal is obtained. Then, in the present embodiment, the components that mainly account for the interference magnetic-field signal are extracted as the overlapping signal components using the first measurement data and the second measurement data, and the extracted overlapping components are removed from the first measurement data.

Accordingly, with the present embodiment, the signals of interest from which the interference due to the interference magnetic-field signals have been removed can be obtained regardless of the relative positions of the site of interest and the source of an interference magnetic-field signal.

In the present embodiment, it is desired that the distance L between the measurable area 120 and the site of interest be equal to or longer than 1 centimeters (cm) when the second measurement data is to be obtained. In other words, in the present embodiment, when the second measurement data is to be obtained, it is desired that the site of interest and the measurable area 120 be separate from each other such that the portion of the site of interest that is farthest from the measurable area 120 is away from the measurable area 120 by at least 1 cm.

When the distance L is shorter than 1 cm, the distribution of the signals of interest included in the second measurement data is similar to the distribution of the signals of interest included in the first measurement data. In such cases, the signals of interest that are included in the second measurement data may be withdrawn from the object of the CSP. In the present embodiment, the distance L is made equal to or longer than 1 cm to prevent the second measurement data from being excluded from the object of the CSP.

Next, the results of measuring the magnetic field of a site of interest by the biomagnetic field measuring device 100 according to the present embodiment are described with reference to FIG. 6A, FIG. 6B, FIG. 7A, FIG. 7B, and FIG. 8.

Figure 6A:
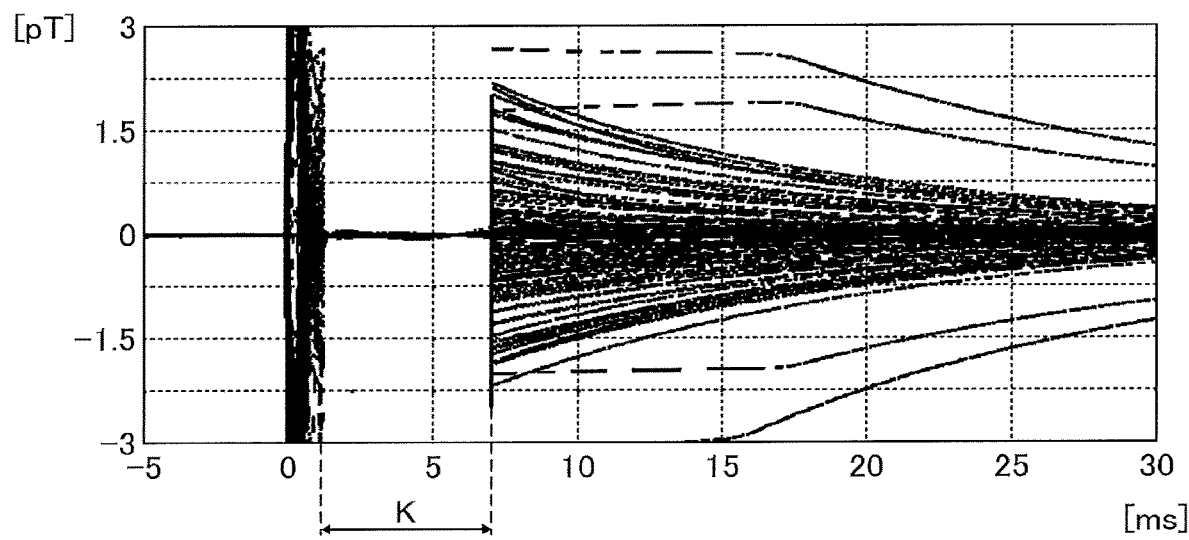
FIG. 6A and FIG. 6B are a first set of diagrams illustrating the signals of interest measured in the first embodiment of the present disclosure.
Figure 6B:
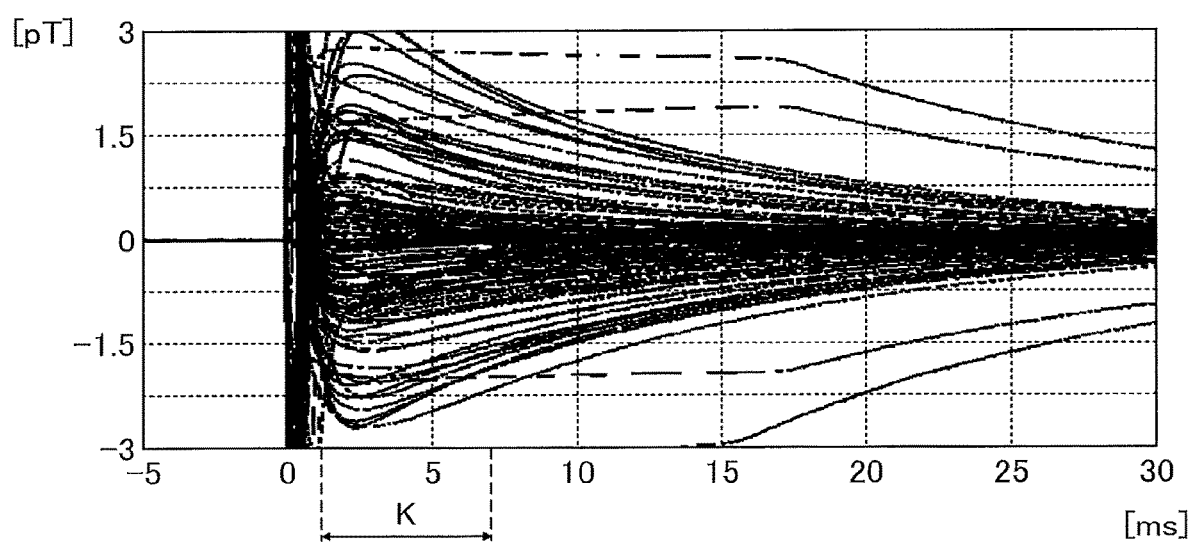

FIG. 6A and FIG. 6B are the first set of diagrams illustrating the signals of interest measured in the first embodiment.

FIG. 6A is a diagram illustrating the signals of interest output from the analyzer 150, according to the present embodiment.

FIG. 6B is a diagram illustrating the first measurement data (i.e., the data from which the interference from an interference magnetic-field signal is not removed), according to the present embodiment.

FIG. 6A and FIG. 6B are diagrams illustrating the results of performing analysis for the section K in the first measurement data by the analyzer 150, where the start point of the section K indicates 1.2 msec after the measurement started and the end point of the section K indicates 7.0 msec after the measurement started.

When the signals in the section K as illustrated in FIG. 6A are compared with the signals in the section K as illustrated in FIG. 6B, the interference magnetic-field signals are removed in the signals of interest in the section K as illustrated in FIG. 6A.

Figure 7A:
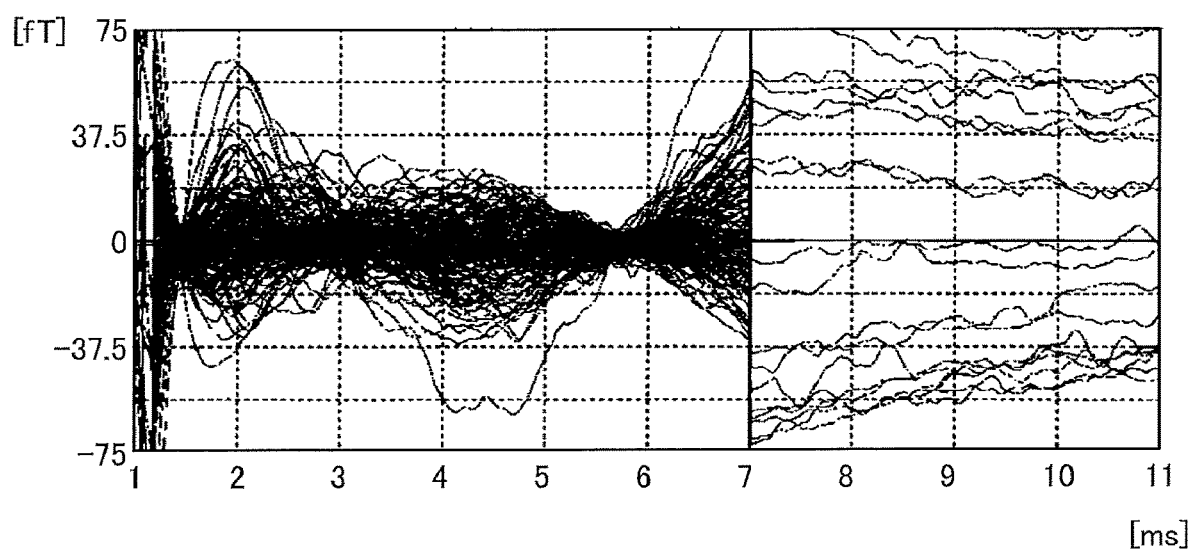
FIG. 7A and FIG. 7B are a first set of diagrams illustrating how the nerve activity is conducted in the first embodiment of the present disclosure.
Figure 7B:
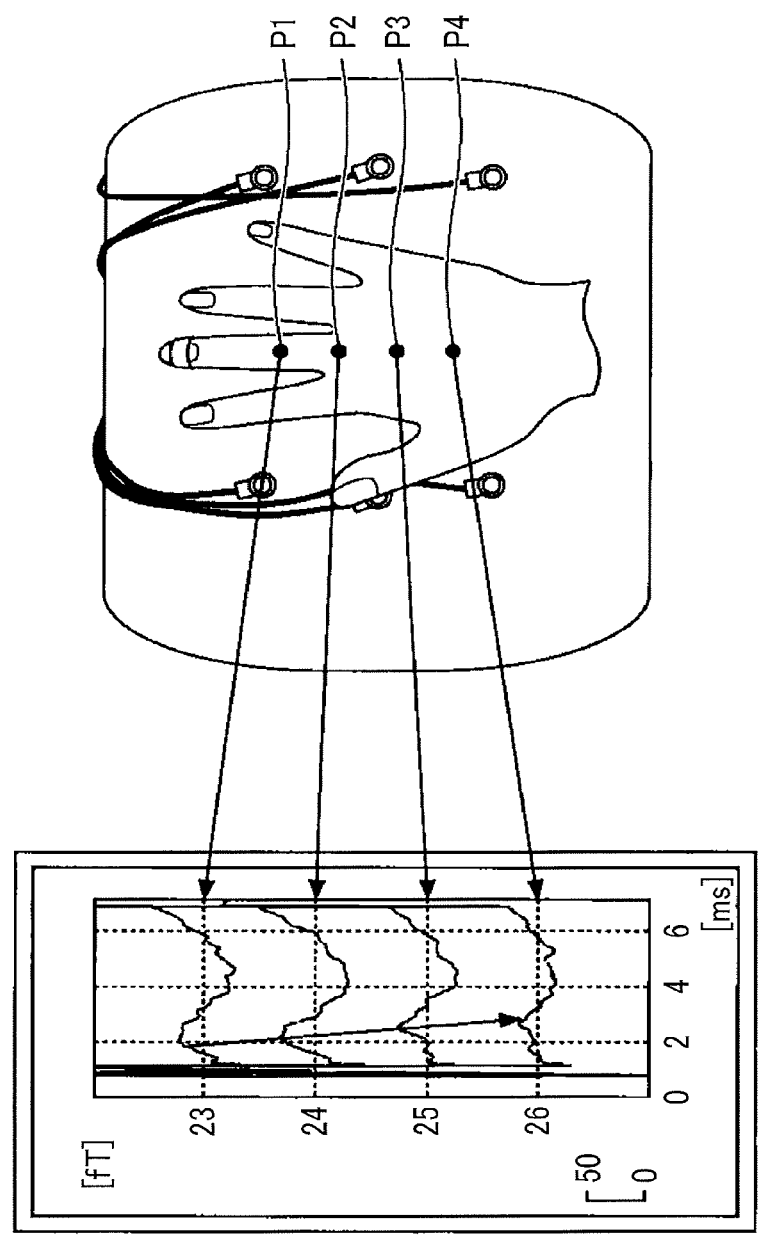

FIG. 7A and FIG. 7B are the first set of diagrams illustrating how the nerve activity is conducted in the first embodiment.

FIG. 7A is a magnified view of the section K as illustrated in FIG. 6A.

FIG. 7B is a diagram illustrating how the nerve activity that is induced by stimuli is conducted, according to the present embodiment.

In FIG. 7B, output signals are extracted from the four sensors that are disposed around the positions P1 to P4 along the nerves of the site of interest, from among the signals that are output from the sensors that are included in the magnetic field detector 110. FIG. 7B illustrates how the peak moves to a proximal side as the time passes by. In other words, the nerve activity is recorded therein.

Figure 8:
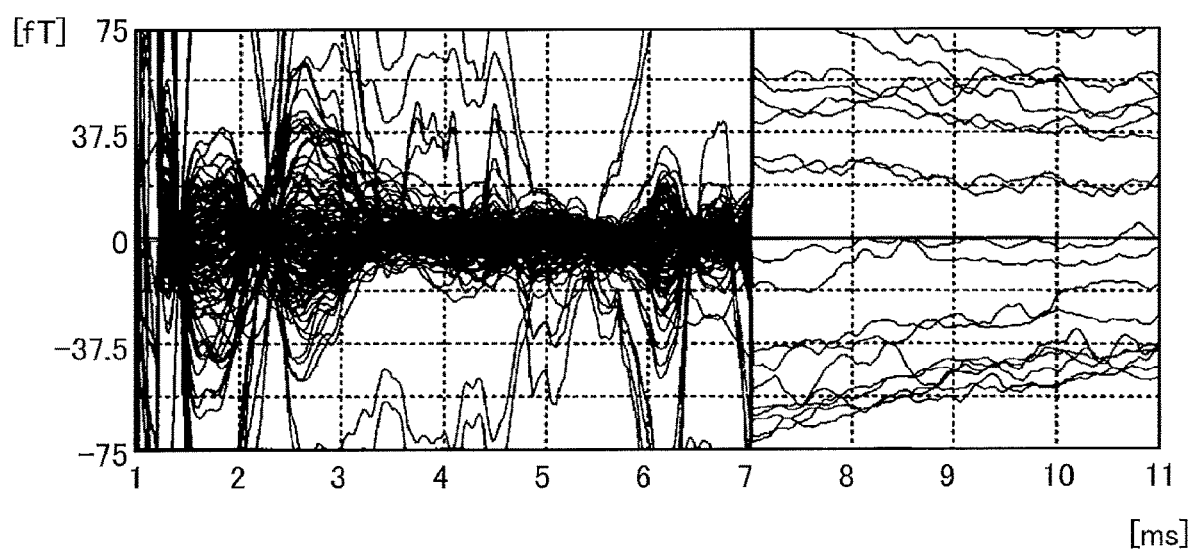
FIG. 8 is a diagram illustrating a control sample of the measurement results in the first embodiment of the present disclosure.

Here, as a control sample, signals of interest are described when the site to which a stimulus is given in the second measurement procedure is also separated from the biomagnetic field measuring device 100 in a similar manner to the site of interest. FIG. 8 is a diagram illustrating a control sample of the measurement results in the first embodiment.

Compared with the example illustrated in FIG. 6A, in the control sample illustrated in FIG. 8, the interference magnetic-field signals are not sufficiently removed even though analysis is performed by the analyzer 150.

In other words, it is desired that the site to which a stimulus is given be arranged at the same position between the first measurement procedure and the second measurement procedure. In view of the above circumstances, it is desired that the separating distance L in the second measurement procedure be determined so as not to move the site of a test object to which a stimulus is given.

As described above, according to the present embodiment, the signals of interest from which the interference due to the interference magnetic-field signals have been removed can be obtained even when the source of an interference magnetic-field signal is disposed near the site of interest.

In the present embodiment, cases in which the site of interest is a palm of a hand are described. However, the site of interest may be a different part of a human body other than the palm of a hand.

Next, cases in which the site of interest is a forearm of the test object P are described with reference to FIG. 9A and FIG. 9B.

Figure 9A:
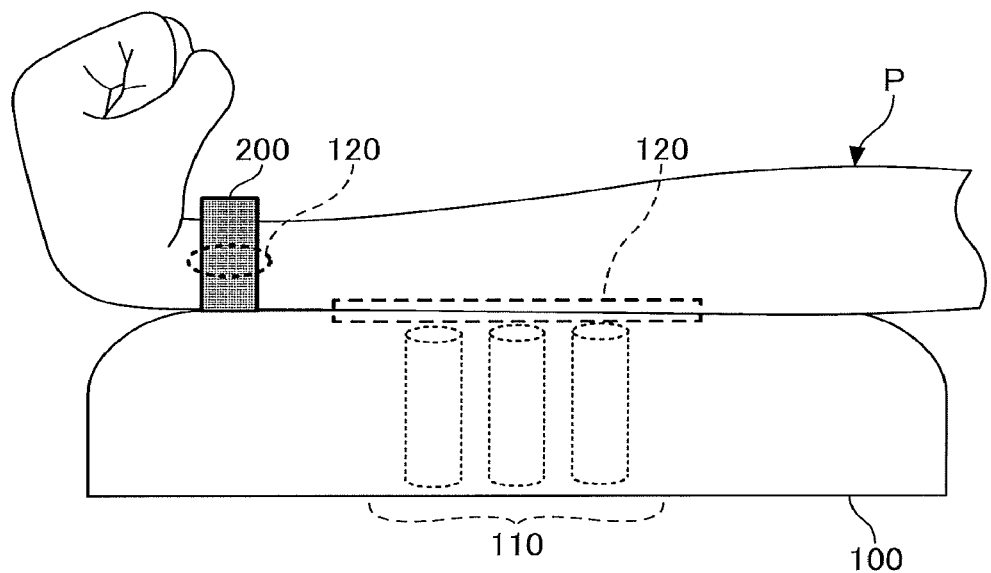
FIG. 9A and FIG. 9B are diagrams illustrating biomagnetic measurement for a forearm, according to the first embodiment of the present disclosure.
Figure 9B:
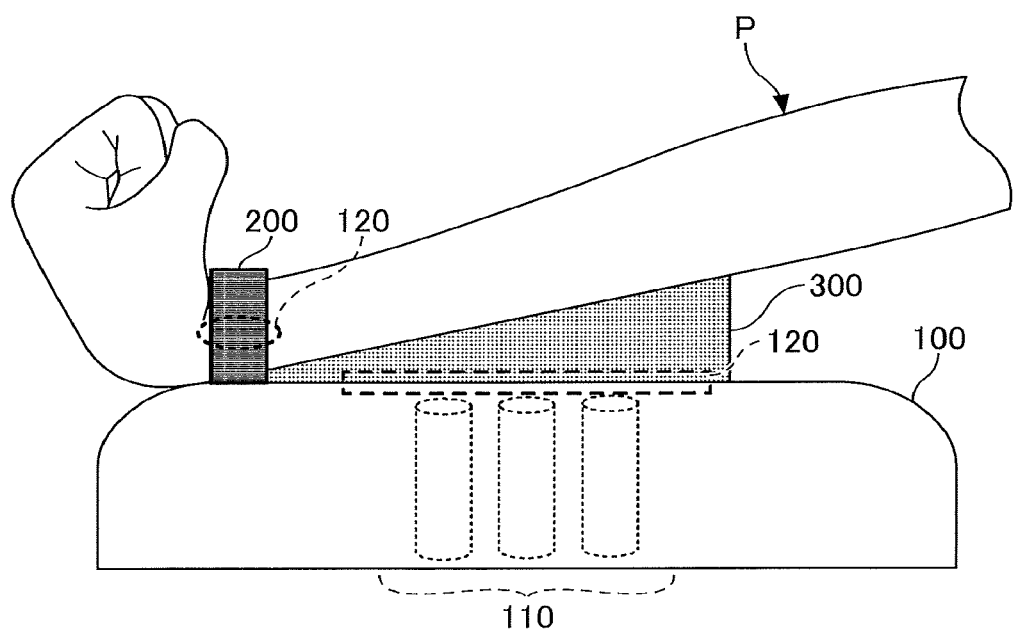

FIG. 9A and FIG. 9B are diagrams illustrating biomagnetic measurement for a forearm, according to the first embodiment.

FIG. 9A is a diagram illustrating how a forearm is measured under the first measurement procedure, according to the present embodiment.

FIG. 9B is a diagram illustrating how a forearm is measured under the second measurement procedure, according to the present embodiment.

In the first measurement procedure as illustrated in FIG. 9A, the nerve stimulator 200 is fixed to the wrist. Then, the first measurement data is obtained as measurement is performed in a state where the site of interest of the forearm is in full contact with the measurable area 120. In this configuration, the source 210 of an interference magnetic-field signal is a contact surface where the nerve stimulator 200 contacts the test object P. Accordingly, the source 210 of an interference magnetic-field signal is around the wrist.

Next, in the second measurement procedure as illustrated in FIG. 9B, the supporting member 300 is disposed between the site of interest and the measurable area 120 without changing the site to which a stimulus is given by the nerve stimulator 200, and the site of interest is separated from the measurable area 120. In the second measurement procedure, measurement is performed in the above state, and the second measurement data is obtained.

Figure 10A:
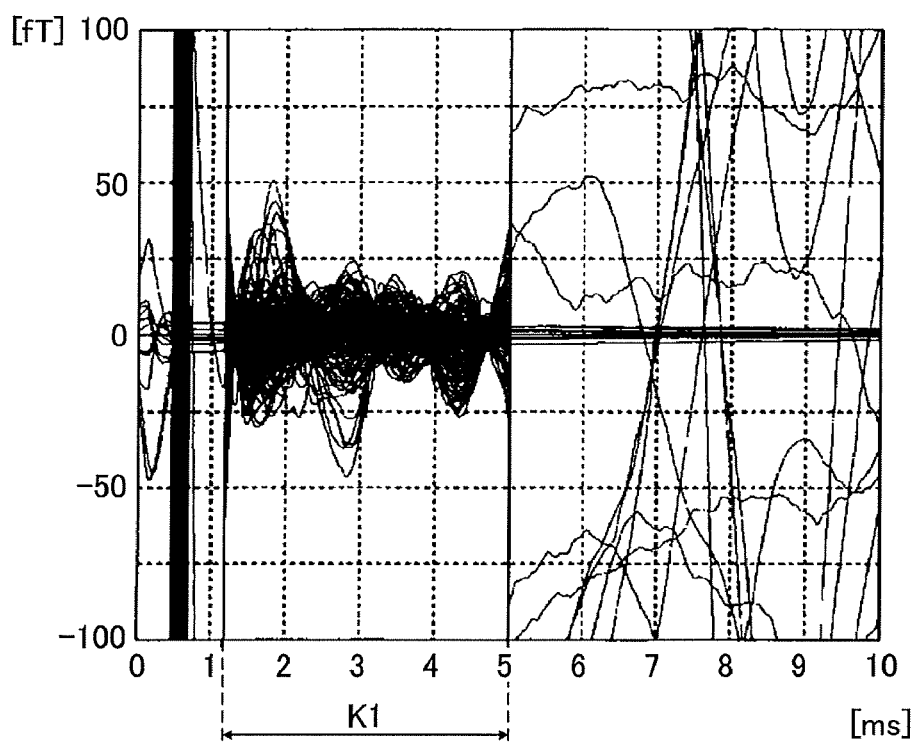
FIG. 10A and FIG. 10B are a second set of diagrams illustrating the signals of interest measured in the first embodiment.
Figure 10B:
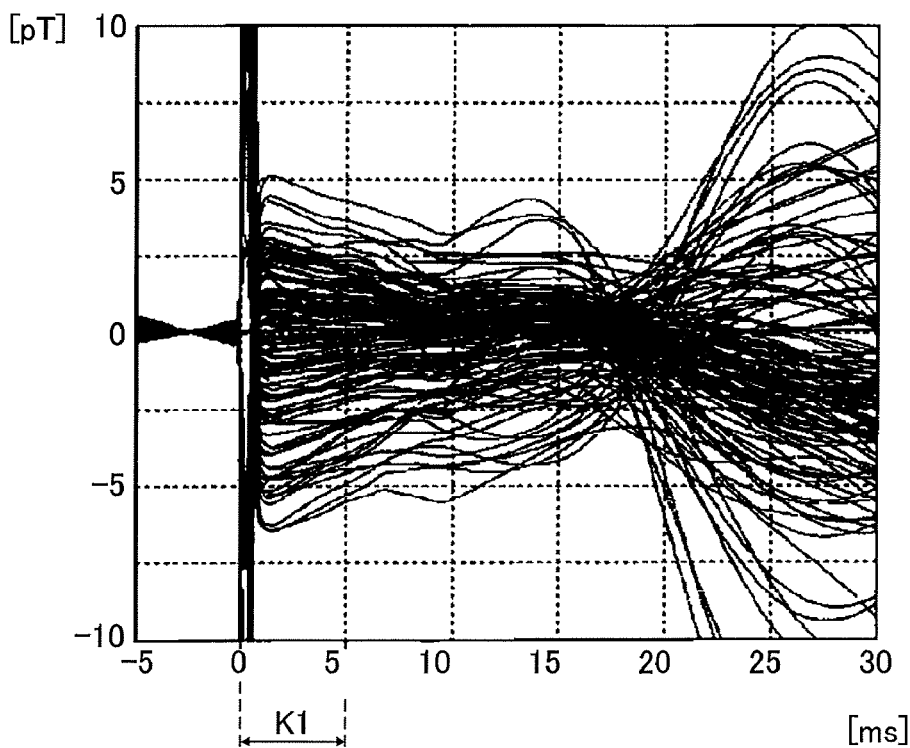

FIG. 10A and FIG. 10B are the second set of diagrams illustrating the signals of interest measured in the first embodiment.

FIG. 10A is a diagram illustrating the signals of interest output from the analyzer 150, according to the present embodiment.

FIG. 10B is a diagram illustrating the first measurement data (i.e., the data from which the interference from an interference magnetic-field signal is not removed), according to the present embodiment.

FIG. 10A and FIG. 10B are diagrams illustrating the results of performing analysis for the section K in the first measurement data by the analyzer 150, where the start point of the section K indicates 1.2 msec after the measurement started and the end point of the section K indicates 5.0 msec after the measurement started.

When the signals of interest in a section K1 as illustrated in FIG. 10A are compared with the first measurement data in the section K1 as illustrated in FIG. 10B, it is understood that the interference magnetic-field signals are removed from the signals of interest in the section K1 of FIG. 10A.

Figure 11:
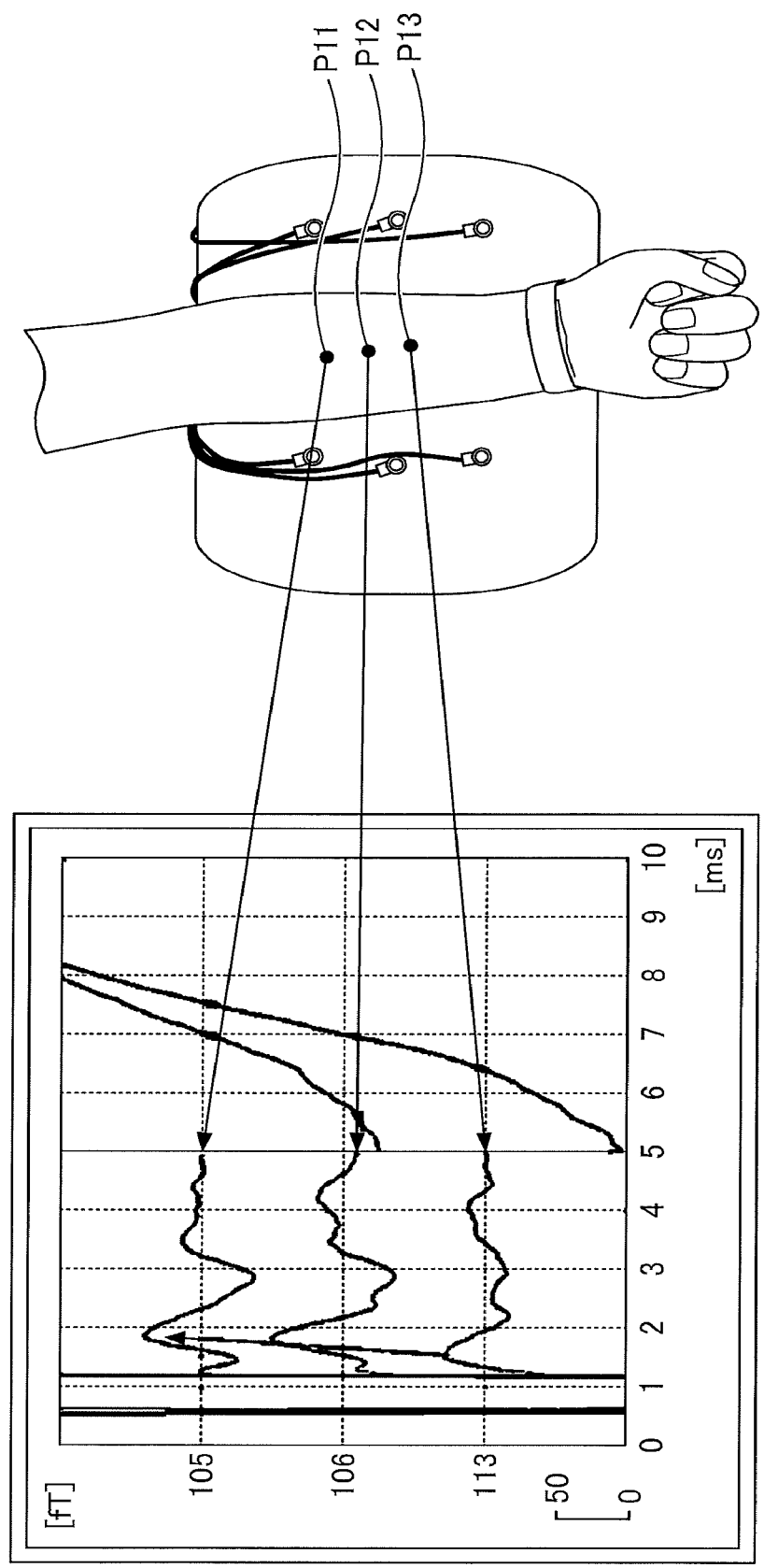
FIG. 11 is a second diagram illustrating how the nerve activity is conducted in the first embodiment of the present disclosure.

FIG. 11 is the second diagram illustrating how the nerve activity is conducted in the first embodiment of the present disclosure.

In FIG. 11, output signals are extracted from the three sensors that are disposed around the positions P11, P12, and P13, from among the signals that are output from the sensors that are included in the magnetic field detector 110. Note that the positions P11, P12, and P13 are arranged along the nerves of the site of interest. FIG. 11 illustrates how the peak moves to a proximal side as the time passes by. In other words, the nerve activity is recorded therein.

As described above, according to the present embodiment, even when the site of interest is a different part of a human body other than the palm of a hand, the signals of interest from which the interference magnetic-field signals have been removed can be obtained.

Accordingly, with the present embodiment, the site of interest and a site to which a stimulus is given may be chosen as desired, and thus application is possible to, for example, diagnosis of various kinds of sickness.

Second Embodiment

A second embodiment of the present disclosure is described below with reference to the accompanying drawings. In the second embodiment, the processes that are performed by the analyzer 150 are different from those in the first embodiment. Accordingly, in the descriptions of the second embodiment as given below, only the differences from the first embodiment will be described. Like reference signs are given to like elements in the second embodiment, and their detailed description is omitted.

Figure 12:
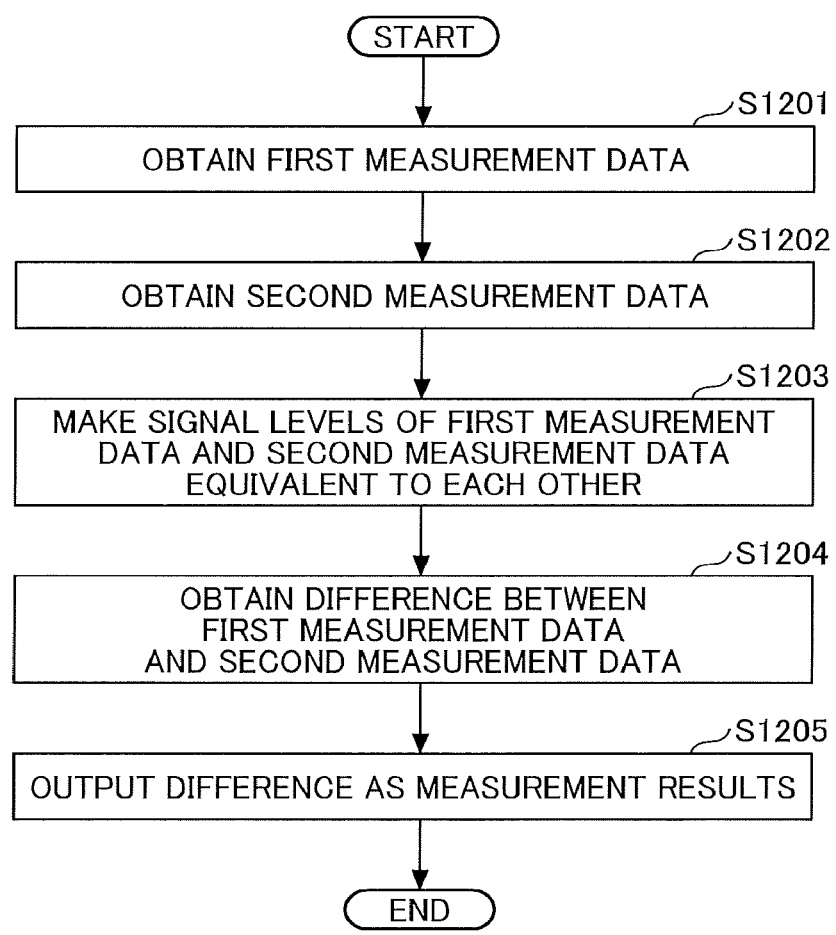
FIG. 12 is a flowchart of the processes that are performed by an analyzer of a biomagnetic field measuring device, according to the second embodiment of the present disclosure.

FIG. 12 is a flowchart of the processes that are performed by the analyzer 150 of the biomagnetic field measuring device 100, according to the second embodiment.

The processes in steps S1201 to S1202 in FIG. 12 are equivalent to the processes in the steps 5501 and 5502 in FIG. 5, and thus their detailed description is omitted.

Once the analyzer 150 obtains the first measurement data and the second measurement data, the analyzer 150 makes the signal levels of the first measurement data and the second measurement data equivalent to each other (step S1203).

Next, the analyzer 150 extracts a signal of the difference between the first measurement data and the second measurement data (step S1204). Then, the analyzer 150 outputs the extracted signal of the difference as a signal of interest (step S1205), and terminates the processes.

As described above, according to the present embodiment, without using the CSP as above, an interference magnetic-field signal can be removed from the signals that are output from the magnetic field detector 110, and the accuracy of the measurement in a biomagnetic field improves.

Third Embodiment

A third embodiment of the present disclosure is described below with reference to the accompanying drawings. In the third embodiment, the functions of the analyzer 150 are provided for an external device outside the biomagnetic field measuring device. In this respect, the third embodiment is different from the first embodiment. Accordingly, in the descriptions of the third embodiment as given below, like reference signs used in the first embodiment are given to like elements in the third embodiment, and their detailed description is omitted.

Figure 13:
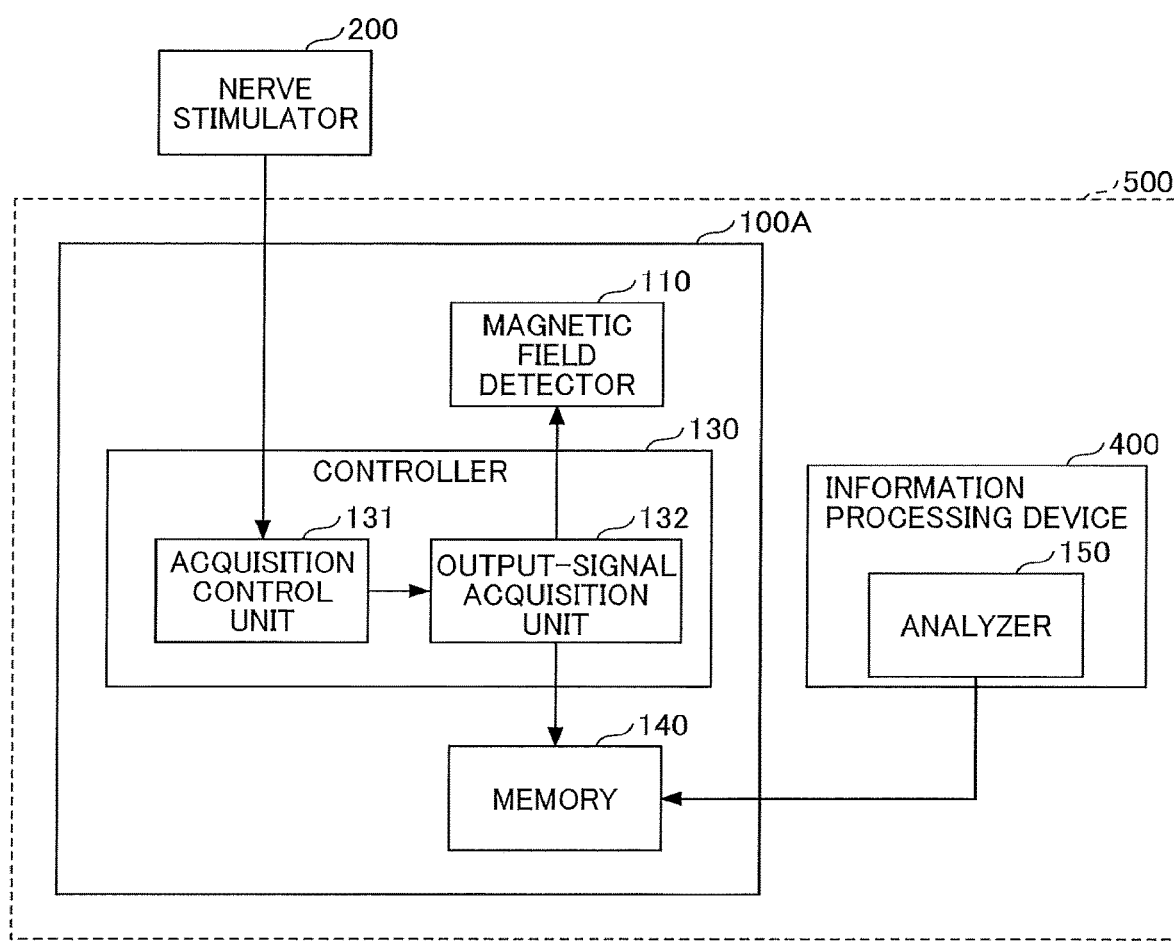
FIG. 13 is a diagram illustrating a biomagnetic field measuring device according to a third embodiment.

FIG. 13 is a diagram illustrating a biomagnetic field measuring device according to the third embodiment.

A biomagnetic field measuring device 100A according to the present embodiment makes up a biomagnetic field measuring system 500 together with an information processing device 400. In the biomagnetic field measuring system 500 according to the present embodiment, the biomagnetic field measuring device 100A and the information processing device 400 can communicate with each other through a wired or wireless connection.

The biomagnetic field measuring device 100A according to the present embodiment includes the magnetic field detector 110, the controller 130, and the memory 140.

The information processing device 400 according to the present embodiment is a general-purpose computer having a processor and memory, and may serve as the analyzer 150. The information processing device 400 according to the present embodiment obtains, from the biomagnetic field measuring device 100A, the first measurement data and the second measurement data stored in the memory 140, and outputs a signal of interest using the first measurement data and the second measurement data. For example, the first measurement data and the second measurement data may be stored in a portable memory, and may be read by the information processing device 400.

As described above, in the present embodiment, the analyzer 150 is provided outside the biomagnetic field measuring device 100A. Due to this configuration, the configuration of the biomagnetic field measuring device 100A can be simplified.

Numerous additional modifications and variations are possible in light of the above teachings. It is therefore to be understood that within the scope of the appended claims, the disclosure of the present invention may be practiced otherwise than as specifically described herein. For example, elements and/or features of different illustrative embodiments may be combined with each other and/or substituted for each other within the scope of this disclosure and appended claims.

What is claimed is:

1. A biomagnetic measurement method, comprising:
    obtaining first measurement data output from a magnetic field detector that detects a magnetic field generated in a subject, in response to a first stimulus provided to a stimulus position of the subject at a first time, in a first state in which a site of interest of the subject is at a first position adjacent to the magnetic field detector;
    obtaining second measurement data output from the magnetic field detector, in response to a second stimulus provided to the stimulus position of the subject at a second time different from the first time, in a second state in which the site of interest of the subject is at a second position away from the magnetic field detector and separated from the first position by a predetermined distance; and
    outputting a signal of interest from which an interference magnetic-field signal component, present in the first and second measurement data, has been removed from the first measurement data using the second measurement data.

2. The method according to claim 1, wherein the interference magnetic-field signal component is a component in common in the first measurement data and the second measurement data and the method further comprises removing the interference magnetic-field signal component from the first measurement data.

3. The method according to claim 1, Wherein the stimulus position of the subject is adjacent to the site of interest.

4. The method according to claim 1, wherein the first stimulus and the second stimulus are generated under a same stimulus condition.

5. The method according to claim 4, wherein the stimulus condition includes at least one of a frequency, a duration in time, and a value of a current.

6. A biomagnetic field measuring device, comprising:
    a magnetic field detector to measure a magnetic field generated in a subject;
    first circuitry configured to obtain
        first measurement data output from the magnetic field detector, in response to a first stimulus provided to a stimulus position of the subject at a first time, in a first state in which a site of interest of the subject is at a first position adjacent to the magnetic field detector, and
        second measurement data output from the magnetic field detector, in response to a second stimulus provided to the stimulus position of the subject at a second time different from the first time, in a second state in which the site of interest of the subject is at a second position away from the magnetic field detector and separated from the first position by a predetermined distance; and
    second circuitry configured to output a signal of interest from which an interference magnetic-field signal component, present in the first and second measurement data, has been removed from the first measurement data using the second measurement data.

7. The biomagnetic field measuring device according to claim 6, further comprising a supporting member disposed on a measurable area of the magnetic field detector in the second state, the measurable area being on a housing of the biomagnetic field measuring device.

8. The biomagnetic field measuring device according to claim 6, wherein the first circuitry and the second circuitry are implemented by a same processor executing program instructions.

9. A biomagnetic field measuring system, comprising:
    a magnetic field detector to measure a magnetic field generated in a subject;
    first circuitry configured to obtain
        first measurement data output from the magnetic field detector, m response to a first stimulus provided to a stimulus position of the subject at a first time, in a first state in which a site of interest of the subject is at a first position adjacent to the magnetic field detector, and
        second measurement data output from the magnetic field detector, in response to a second stimulus provided to the stimulus position of the subject at a second time different from the first time, in a second state in which the site of interest of the subject is at a second position away from the magnetic field detector and separated from the first position by a predetermined distance; and
    second circuitry configured to output a signal of interest from which an interference magnetic-field signal component, present in the first and second measurement data, has been removed from the first measurement data using the second measurement data.

10. The biomagnetic measurement method of claim 1, wherein the outputting step comprises removing the interference magnetic-field signal component by subtracting the second measurement data from the first measurement data over a determined time period.

* * * * *